(12) United States Patent
Liebing (10) Patent No.: US 10,518,010 B2
(45) Date of Patent: Dec. 31, 2019

(54) CATHETER DEVICE, COMPRISING A VALVE FOR CONTROLLING A FLUID FLOW THROUGH A CATHETER

(71) Applicant: ECP ENTWICKLUNGSGESELLSCHAFT MBH, Berlin (DE)

(72) Inventor: Reiner Liebing, Berlin (DE)

(73) Assignee: ECP ENTWICKLUNGSGESELLSCHAFT MBH, BerlinAmtsgericht Berlin (Charlottenburg) (DE)

( * ) Notice: Subject to any disclaimer, the term of this patent is extended or adjusted under 35 U.S.C. 154(b) by 219 days.

(21) Appl. No.: 15/545,003

(22) PCT Filed: Jan. 22, 2016

(86) PCT No.: PCT/EP2016/051358
§ 371 (c)(1),
(2) Date: Jul. 20, 2017

(87) PCT Pub. No.: WO2016/116608
PCT Pub. Date: Jul. 28, 2016

(65) Prior Publication Data
US 2018/0133380 A1    May 17, 2018

(30) Foreign Application Priority Data

Jan. 22, 2015   (EP) .................................... 15152201
Jan. 22, 2015   (EP) .................................... 15152205

(51) Int. Cl.
*A61M 1/10*      (2006.01)
*A61M 39/22*    (2006.01)
(Continued)

(52) U.S. Cl.
CPC .......... *A61M 1/1087* (2014.02); *A61M 1/102* (2014.02); *A61M 1/1039* (2014.02);
(Continued)

(58) Field of Classification Search
CPC .. A61M 1/1087; A61M 1/1024; A61M 1/102; A61M 1/103; A61M 1/1039;
(Continued)

(56) References Cited

U.S. PATENT DOCUMENTS

| 6,245,007 B1 | 6/2001 | Bedingham et al. |
| 2004/0055652 A1 | 3/2004 | Erickson |

(Continued)

FOREIGN PATENT DOCUMENTS

| DE | 41 23 091 A1 | 1/1993 |
| DE | 42 24 389 A1 | 1/1994 |

(Continued)

*Primary Examiner* — Paula J Stice
(74) *Attorney, Agent, or Firm* — White & Case LLP (57) ABSTRACT

The invention relates to a catheter device (100) comprising a catheter (68) for insertion into a living being and at least one lumen (69, 70, 74, 79) for guiding a fluid flow within a section of the catheter device, and comprising a valve for controlling a fluid flow, in particular through a catheter, having a valve control chamber (12, 12a), into which an inlet opening (1a) of an inlet channel (1) and an outlet opening (2a) of an outlet channel (2) open, and further having a closure element (5, 13, 17) which can be moved in the valve control chamber (12, 12a) in a controlled manner and which, in at least a first position (I), closes the outlet opening (2a), in at least a second position (II) closes the inlet opening (1a), and which, in at least a third position (III), keeps open a connecting channel between the inlet opening (1a) and the outlet opening (2a), a valve train (A, A', B, B', 3, 14, 18) being provided and optionally moving the closure element (5, 13, 17) to at least the first, second or third position, and (Continued)

the at least one lumen (68, 70, 74, 79) being fluidically connected to the inlet channel or the outlet channel.

17 Claims, 10 Drawing Sheets

(51) Int. Cl.
*A61M 1/12* (2006.01)
*A61M 25/00* (2006.01)

(52) U.S. Cl.
CPC ............ *A61M 1/122* (2014.02); *A61M 1/125* (2014.02); *A61M 25/0043* (2013.01); *A61M 39/22* (2013.01); *A61M 39/223* (2013.01); *A61M 1/101* (2013.01); *A61M 1/1024* (2014.02); *A61M 1/1034* (2014.02); *A61M 2039/224* (2013.01); *A61M 2039/226* (2013.01); *A61M 2205/0272* (2013.01); *A61M 2205/7545* (2013.01)

(58) Field of Classification Search
CPC ...... A61M 1/101; A61M 1/122; A61M 1/125; A61M 25/0046; A61M 39/22; A61M 39/223; A61M 2039/224; A61M 2039/226; A61M 2205/0272; A61M 2205/7545
See application file for complete search history.

(56) References Cited

U.S. PATENT DOCUMENTS

| | | |
|---|---|---|
| 2010/0331753 A1 | 12/2010 | Gandini |
| 2012/0178985 A1 | 7/2012 | Walters et al. |
| 2014/0261717 A1 | 9/2014 | Egley et al. |

FOREIGN PATENT DOCUMENTS

| | | |
|---|---|---|
| DE | 203 02 911 U1 | 7/2004 |
| WO | WO-89/05668 A2 | 6/1989 |
| WO | WO-01/17581 A2 | 3/2001 |
| WO | WO-2008/101352 A1 | 8/2008 |
| WO | WO-2012/122627 A1 | 9/2012 |

CATHETER DEVICE, COMPRISING A VALVE FOR CONTROLLING A FLUID FLOW THROUGH A CATHETER

CROSS-REFERENCE TO RELATED APPLICATIONS

This application is a United States National Stage filing under 35 U.S.C. § 371 of International Application No. PCT/EP2016/051358, filed Jan. 22, 2016, which claims the benefit of European Patent Application No. 15152201.8, filed Jan. 22, 2015, and European Patent Application No. 15152205.9, filed Jan. 22, 2015, the contents of all of which are incorporated by reference herein in their entirety.

The invention lies in the field of mechanics and is particularly advantageously applicable to the field of medical technology. It relates in particular to a valve which even at different pressure conditions permits a reliable blocking of a fluid flow through a catheter.

Various shut-off valves for the control of fluid flows are known from the state of the art. An industrially developed disposable shut-off valve is disclosed for example in DE 20 2013 104711 A1. A simple check valve is known for example from DE 11 2009 003 676 T5. Such check valves are applied for example in motor vehicle technology. Such shut-off valves basically have a very restricted area of application, wherein problems either occur at overpressure or underpressure or in the case of pressure fluctuations, since such valves are often only designed for a narrow pressure range. However, a separation of media is moreover absolutely necessary, which is to say the actual fluid channel including the blocking location must be hermetically closed from the other elements of a valve, such as the drive elements for example, in the case of application in the medical field, but also in other special fields.

Moreover, a simple cleaning and sterilisation possibility or selectively a simple exchangeability in the case of disposable components being used is important for applications in the field of medical technology.

Against the background of the state of the art, it is therefore the object of the invention to create a catheter device or a valve, which permits a reliable shutting and opening of a fluid channel at low fluid throughputs, also under different pressure conditions.

This object is achieved by the features of the invention according to the patent claims. Advantageous embodiments of the invention are specified in the dependent claims.

This firstly relates to a catheter device, comprising a catheter for introduction into a living being, as well as at least one lumen for leading a fluid flow with a part of the catheter device and well as comprising a valve for the control of a fluid flow in particular through a catheter, with a valve control space, in which a feed channel runs out with a feed opening, and a discharge channel runs out with a discharge opening, and with a closure element which is moveable in a controlled manner in the valve control space and which in at least one first position closes the discharge opening, in at least one second position closes the feed opening and in at least one third position holds open a connection channel between the feed opening and the discharge opening, wherein a valve drive is provided, which moves the closure element selectively at least into the first, second or third position, wherein the at least one lumen is connected in a fluid-conducting manner to the feed channel or to the discharge channel.

As is explained in more detail once again further below, a very precise leading of rinsing fluid is possible with the catheter device, this being the case with regard to the rinsing direction as well as with regard to the rinsing volumes and rinsing flows in the catheters. This is particularly effected against the background of flexible rotatable shafts, which in particular have a suction effect or changing pressure conditions, depending on the length and the location of installation. Moreover, a perfect functioning of the valves is of utmost importance indeed in this field of medical technology. In particular, the coupling to a separating device for removing contamination and wear debris, for example metal wear debris, out of the rinsing fluid is also controllable. This can be the case for example if a temporary direction reversal for cleaning makes sense in the case of a "through-rinsing" of a separating device (thus of a device for capturing/trapping wear debris, etc.)

Examples of such a separating device for example are explained in the parallel ECP 46 PCT (file number not yet known) of ECP GmbH which has been filed on the same day. The priority of both prior applications EP 15152201.8 and EP 15152205.9 is moreover claimed. The contents of the disclosure of all three patent applications in their initially filed form are hereby incorporated in their entirety into the present application by reference ("incorporation by reference").

One embodiment envisages the catheter comprising a rotatable shaft. This for example is flexible, in particular flexible in a manner such that it can be adapted to a curvature of a human aortic arch, thus that a pump head at the tip of the flexible shaft is introduced into the ventricle of the heart, for example on introducing a respective shaft into the femoral artery and leading it further along the aorta, and that the catheter automatically adapts to the curvature of the aortic arch on pushing the catheter in the direction of the rising aorta.

In an embodiment, the drive device is selected outside the living being (thus outside the femoral artery in the above example), and the rotatable shaft runs into the femoral artery for example to into the left ventricle for the drive of a pump head of a catheter pump (heart pump) which is positioned there.

A further embodiment envisages the catheter comprising more than one lumen, wherein at least one lumen is designed for the leading of fluid in the distal direction and at least one lumen for leading the fluid in the proximal direction.

In an embodiment, between 10 and 90 percent of the fluid flow led in the distal direction and in a first lumen, can be led back in another lumen and in the proximal direction. With so called "Y-rinsing", thus a fluid flow is delivered in the distal direction, a part of the rinsing fluid for example gets into the heart at the distal end of the catheter and another part of the rinsing fluid then exits again through the respective other lumen. Yet more complex embodiments are possible, with which the drive device (i.e. the drive which is located for example outside the body) is additionally yet supplied with a fluid flow, in order for example to remove wear debris in the region of the bearings etc. out of the catheter device.

For this reason, embodiments envisage one, two, three or also more valves being provided, in order for example to carry out more complex rinsing (flushing) procedures or deliberate reversals of the rinsing direction (for cleaning a separating device for example).

One embodiment envisages several valves, for example two valves being provided, wherein the discharge of the first valve is connected to feed to the drive device of the catheter device, and a second valve being present, wherein the feed of the second valve is connected to a lumen of the catheter which leads fluid in the proximal direction.

Different embodiments of valves in a catheter device 100 are shown in the specific description part. This in particular relates to the embodiments 8, 9, 10, 11, and 12.

It is also to be mentioned that the valves are designed such that a valve drive of the closure element is separable, i.e. can be separated from the remainder of the arrangement in a tool-free manner, above all to permit a simpler exchange and to ensure the sterility at low costs, even with a multiple use of parts of the arrangement.

It is also to be mentioned that the valve drive can be effected in any manner. Apart from magnetically acting drives, the drive can also be effected in a purely mechanical manner, and it can also be effected electrically or also inductively, and here any drives permitting the man skilled in the art to achieve a movement of the closure element into the first, second and/or third position are possible.

Amongst other things, the application also relates to a valve for the control of a fluid flow through a catheter, with a valve control space, in which feed channel runs out with a feed opening, and a discharge channel runs out with a discharge opening, and with a closure element which is movable in a controlled manner in the valve control space and which in at least one first position closes the discharge opening, in at least one second position closes the feed opening and in at least one third position holds open a connection channel between the feed opening and the discharge opening, wherein a valve drive is provided, which moves the closure element selectively into the first, second or third position. In one design, different valve gap sizes can be activated for the control of a flow, in the third or further valve positions.

The valve can block the fluid flow by way of closing the discharge opening as well as by way of closing the feed opening, due to the design. The terms feed channel and discharge channel are selected such that the feed channel with its run-out indicates the channel which acts as a feed channel under normal or statistically the most frequent circumstances and pressure conditions. The term discharge channel is defined analogously.

On account of this, with a pressure in the feed channel which is higher than in the discharge channel, as well as with a pressure in the discharge channel which is higher than in the feed channel, in each case there is the possibility of assisting the closure forces and thus the sealed seating of the closure body, on account of the pressure difference, by way of the closure body closing the discharge opening given an overpressure in the feed channel, whereas the closure body closes the feed opening given an excess pressure in the discharge channel. In each of these cases, the closure body is held in the closure position by way of the pressure difference between the valve control space and the respectively closed channel, additionally to the mechanical drive forces.

Since the feed channel in certain cases can function as a discharge channel and vice versa, one could also simply indicate the feed channel as a first channel and the discharge channel as a second channel.

The reliable sealing is particularly important in such systems in which alternating pressure conditions or ones changing over the longer term can prevail. Such conditions for example prevail in catheters which are used for leading mechanically drivable, rotating shafts and/or for rinsing such catheters. Usually, a very low fluid throughput is desired when rinsing or flushing catheters leading a rotating shaft and this very low fluid throughput, amongst other things, leads to wear particles of the shaft being moved further only in a defined direction. Such rotating shafts are often manufactured from a bundle of twisted wires, wherein the bundle has a spiral shape at its outer contour. This spiral shape in the case of a rapid rotation of the shaft accomplishes a delivery effect of the rinsing fluid surrounding the shaft, so that a suction effect occurs additionally to the actual revolving movement of the rinsing fluid which is effected by the rinsing agent pump. This suction effect changes with time, since the contour of the shaft changes with time due to the wearing and abrasive friction. Changing pressure conditions which could even lead to a reversal of the rinsing agent flow occur in corresponding rinsing catheters on account of this. Thereby, with a valve according to the invention, one seeks the possibility of achieving a reliable blocking/control of such a fluid flow, independently of the pressure conditions. As stated above, the possibility arises of achieving a closure of the respective fluid channel by way of selective closure of the feed opening or the discharge opening (or: first opening or second opening), depending on the pressure gradient, wherein the respective closed opening can be selected according to the position, in which the closure position of the closure element at the opening is stabilised by the pressure gradient.

Designs envisage at least parts of the valve being conceived as disposable components. This makes sense for example in the field of medical technology. Fluid-leading components (for example the valve control space) can be exchangeable as disposable components in this manner. Expensive components such as e.g. the valve drive of the closure element which preferably do not come into direct contact with the fluid are envisaged as reusable components. Thus for example it is possible for the valve control space to be part of a catheter, in particular of a catheter hose for example of plastic material. Systems which operate in a contact-free manner (e.g. magnetically, inductively) or utilise elastic characteristics e.g. of the valve control space, in order to transmit drive forces can be considered as valve drives for example.

One design envisages the third position of the closure element lying between the first and the second position.

This has the effect that a release of the fluid channel is rendered possible from each of the closure positions by way of a minimal movement of the closure element, and that each of the two closure positions can be reached from the third position in a rapid and reliable manner and by way of a minimal movement of the closure element.

One can further envisage the valve control space being closed off in a fluid-tight manner on all sides with the exception of the feed opening and the discharge opening.

This design effects a complete separation of the media, so that the elements of the valve drive do not come into contact with the actual fluid to be controlled.

This can be achieved for example by way of the closure element comprising a movable membrane which closes off the valve control space in a fluid tight manner and which is deflectable in a manner such that the feed opening or the discharge opening can be selectively closed by parts of the membrane The membrane which is peripherally connected in a fluid-tight manner to the remaining parts of the valve control space, in particular bonded or welded, in the non-deflected condition forms a closure of the valve control space. The fluid to be controlled can flow past the membrane between the feed opening and the discharge opening or vice versa. The membrane is thereby designed in an elastically or plastically deformable manner, so that it can be deflected, and specifically to such an extent that it or part of it can be selectively brought in front of one of the two openings, the feed opening or the discharge opening, and can be pressed against this opening. A closure of the feed opening or the discharge opening is achieved by way of this. The membrane is relaxed for opening the respective feed opening or discharge opening, so that in the ideal case it moves into its initial condition by itself or due to its intrinsic tension.

For this, an advantageous design of the invention envisages a drive lever of the valve drive deflecting the membrane at least into the first and the second position.

The drive lever thus engages below the membrane and deflects this to such an extent that it is clamped between the feed opening or the discharge opening and the drive lever, and closes the respective opening. If the drive lever of the valve drive is moved back, the membrane then releases again from the respective opening.

The drive lever thereby at its end pressing against the membrane can have a spherical or ellipsoidal shape for example, which is particularly well suited for the closure of an opening in the valve control space amid the interposing of the membrane.

A further advantageous design of the invention can envisage the closure element being driveable by way of a magnetically acting valve drive.

It is possible for example to completely separate the valve itself from the drive unit by way of such a design, for example by way of the valve control space being separated from the magnetic drive by a gas-impermeable or fluid-impermeable wall. The complete valve body which surrounds the valve control space can once again be separated from the elements producing the magnetic fields for the drive, by an intermediate media-separating wall.

The part of the drive lever which is away from the valve control space can be magnetically designed and be deflectable by way of an external magnet for example.

The invention can moreover be advantageously designed such that the closure element arranged in the valve control space is magnetically active and interacts with a magnetic field of the valve drive.

In this case, the closure element or a part of the closure element can consist of a magnet body which for example can be magnetised or can at least consist of a ferromagnetic material and be driven in the field of an external magnet. In this case, the magnetically active part of the closure element is covered with a fluid-impermeable layer which is not magnetically active, so that the fluid, whose flow through the valve is to be controlled, does not come into contact with the magnetically active part.

A further advantageous design envisages the valve control space as well as the parts of the valve drive which are mechanically connected to the closure element, with the exception of the feed opening and discharge opening being closed off in a fluid-tight manner and in particular being separable from a magnetic field producing device of the valve drive.

Due to this design, it is possible for example to separate (which means preferably to separate/to decouple in a destructive-free manner) a part of the valve which comprises the valve control space and, as the case may be, a closure body or parts of the closure body, from the magnetic field production device with little effort and for it to be replaced as a disposable component. The magnetic field production device for its part can then be used several times.

A further advantageous design of the invention envisages the closure element being moved by an elastic spring element, preferably into the third position.

The closure element can be held in the third position by the elastic spring element, for example a helical spring, and be brought by a drive into the first or second position against the force of the spring. After switching off the valve drive, one envisages the elastic spring element automatically moving the closure element into the third position. In this manner, one succeeds in the closure element not being subjected to an external force action and thus in the valve remaining stationary in the opened condition, in the event of the failure of the electrical supply, inasmuch as electromagnetic are used for the drive. The release of the closure element from the first position and the second position is moreover assisted by the elastic spring element.

The invention can moreover be advantageously designed by way of a magnet being provided as part of a separating device directly on the valve control space, in particular in the inside of the closure element. In this case, magnetic and magnetisable particles can be bound by the magnet of the separating device, in the valve control space, so that they are kept way from the sealing surfaces of the valve. Thereby, in particular one can envisage the magnet/magnets being provided separately from and in particular distanced to the drive armatures of the valve drive.

However, one can also envisage the magnet of the separating device being combined or connected to one or more magnets of the valve drive, or a first functional surface of a magnet can serve for the separation of particles, whereas other functional surfaces can serve for the valve function.

The invention can moreover relate to a protective device for a valve which is in connection with a flowing fluid, characterised in that a separating device for holding back particles located in the fluid and with at least one magnetic element is provided along the flow channel for the fluid, in particular a catheter, in a manner distanced to the valve and in particular separated from this.

The separating device can advantageously be provided upstream of the valve with respect to the predominant flow direction of the fluid, but the two mentioned elements can also be simply provided subsequently to one another, in particular distanced to one another, for example also constructionally separated from one another, for example in the form of two separate construction elements with different housings.

The valve can be free of magnetic or magnetically acting elements and for example as a whole be non-magnetic. It can comprise a sealing surface, which is to be protected from particles.

The valve can also comprise magnetic components, such as a drive magnet or an armature. The magnet element of the separating device can be a magnet which is separated from the magnetic components of the valve, or a functional surface of a magnetic construction element which exclusively has the function of particle separation, wherein other functional surfaces of the magnetic construction element can carry out other functions of the valve such a drive function for example. In this latter mentioned case, the magnet element of the separating device can be combined with a magnetic construction element of the valve, be joined together with this, grouped together with this and in particular also be grouped together in a housing.

The functional surface of the separating device can thus capture and bind particles, in particular magnetic and/or magnetisable particles, before they get to the valve and thus compromise the valve function, for example the sealing function of the sealing surfaces.

The invention is hereinafter represented and explained hereinafter, by way of embodiment examples in the figures of a drawing.

Thereby are represented.

Figure 1:
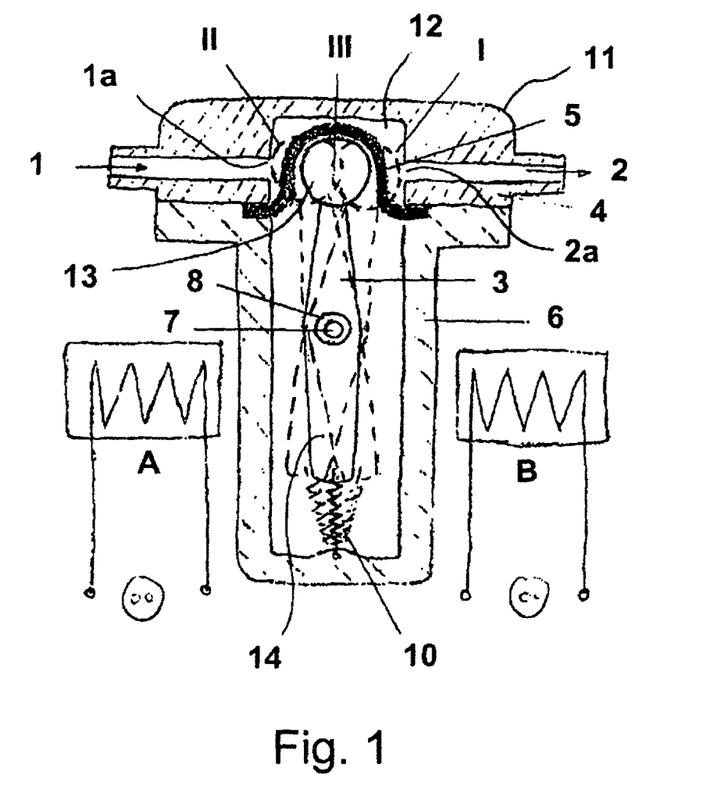
FIG. 1 a first embodiment of a valve with a magnetic valve drive, in a schematic cross section, FIG. 2 the valve arrangement of FIG. 1, in a three-dimensional view, FIG. 3 in a schematic section, a second embodiment of a valve according to the invention, FIG. 4 a view of an elastic spring element, FIG. 5 a three-dimensional view of the valve arrangement of FIG. 3, FIG. 6 a valve which is connected to a separating device, FIG. 7 a further valve connected to a separating device, FIG. 8 a drive unit for a functional element which can be driven by way of a shaft rotating in a catheter, FIG. 9 a modification of a drive unit according to FIG. 8, FIG. 10 and FIG. 11 in each case, further designs of drive devices for shafts rotating in a catheter as well as FIG. 12 a modification of a drive unit according to FIG. 9

FIG. 1 schematically shows a valve body 11 with a feed channel 1, a discharge channel 2 as well as a drive lever 3 which deflects a membrane 5. The membrane 5 closes the valve control space 12 which is located within the valve body 11, in a fluid-tight manner, and can be pressed by a spherical end 13, selectively against the feed opening 1a or the discharge opening 2a, in order to either close the feed channel 1 or the discharge channel 2.

The drive lever 3 is pivotable about a shaft 7, which with spacer sleeves 8 is mounted in the drive housing 6. The drive lever 3 is represented once in an unbroken manner in the third position III, in which it leaves open a connection channel between the feed opening 1a and the discharge opening 2a, as well in a dashed manner in a first position I, in which the spherical end 13 closes the discharge opening 2a by way of the membrane 5, and also dashed, in a second position II, in which the drive lever closes the feed opening 1a by way of the membrane 5.

The elastic spring element 10 is represented as a helical spring in the drive housing 6 in the lower part, and this helical spring connects the end of the drive lever 3 which is away from the membrane to the base of the housing 6 and thus holds the drive lever in the third position III.

Two electromagnets A, B are represented on both sides of the drive housing 6 and these, when they are subjected to a current, produce a magnetic field which acts upon the lower part 14 of the drive lever 3 and moves this into the first position I or into the second position II depending on the direction of the magnetic forces. The lower part 14 of the drive lever 3 is designed in a magnetically active manner for this purpose, either as a ferromagnetic, magnetisable or as a magnetised component.

Figure 2:
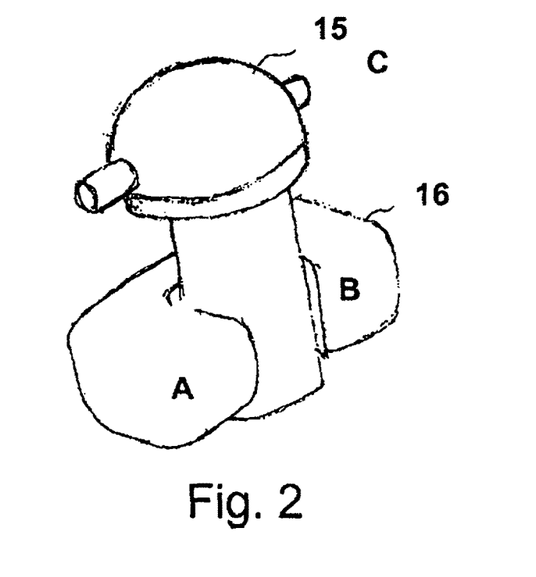

FIG. 2 in a three-dimensional view shows a first housing 15 which comprises or accommodates the valve body with the valve control space as well as the membrane and at least parts of the drive lever 3 and in particular also the drive housing 6. The magnets A, B are arranged in a second housing 16 which is movable with respect to the first housing 15, in particular can also be separated from this. One can envisage both housings 15 16 being connected, for example the first housing 15 being able to be snapped or locked in a holder of the second housing 16. However, it has been found to be advantageous if the first housing 15 is separately removable, so that the parts of the valve device which are contained in the housing 15 can be exchanged separately and in particular can be treated as a disposable valve part.

Figure 3:
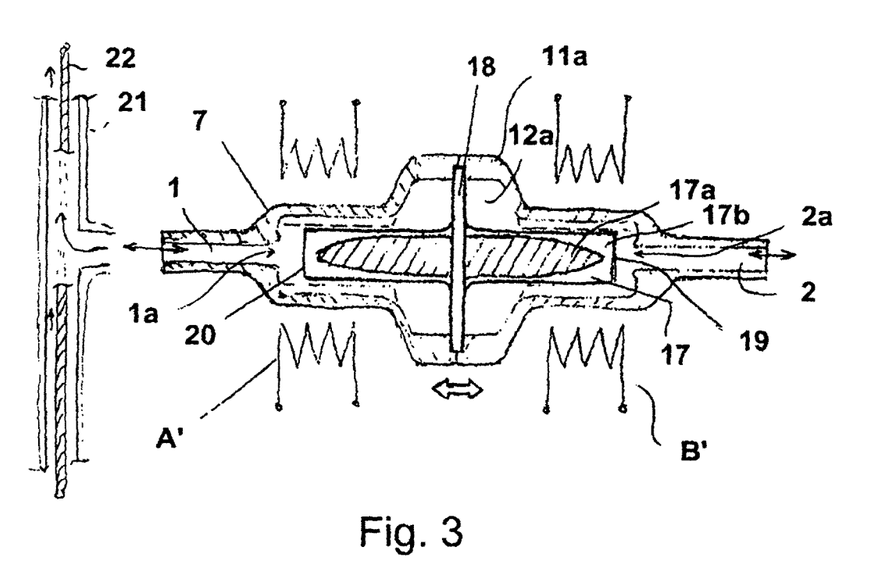
Figure 4:
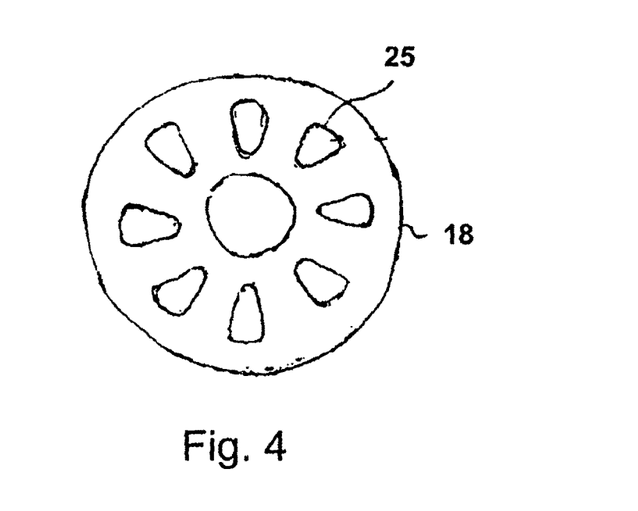

A valve arrangement with a valve body 11a which encloses a valve control space 12a, in which a closure body 17 is movably mounted, is shown in FIG. 3. The closure body 17 comprises a magnetically active core 17a and an encasing 17b, in particular of a plastic, which encloses or encases the core 17a, and is connected to a bearing washer 18. The bearing washer is represented in a plan view in FIG. 4. It is mounted on the valve body 11a at its periphery and as a whole is elastic, so that it holds the closure body 17 in the represented middle position. The bearing washer 18 comprises several openings 25 which permit the through-flow of the fluid to be controlled by the valve.

The ends 19, 20 of the closure body 17 are shaped and designed such that they can close the feed opening 1a or the discharge opening 2a, with a corresponding deflection of the closure body 17 and with a resilient deformation of the bearing washer 18.

For this purpose, the encasing 17b of the closure body 17 can consist of an elastic material, in particular of an elastomer for example. The magnetic core 17a of the closure body 17, by way of the magnet devices A', B' can be subjected to a force which pulls the closure body 17 either in the direction of the feed opening 1a or in the direction of the discharge opening 2a, in order to bring the valve into the first or the second closure position.

Figure 5:
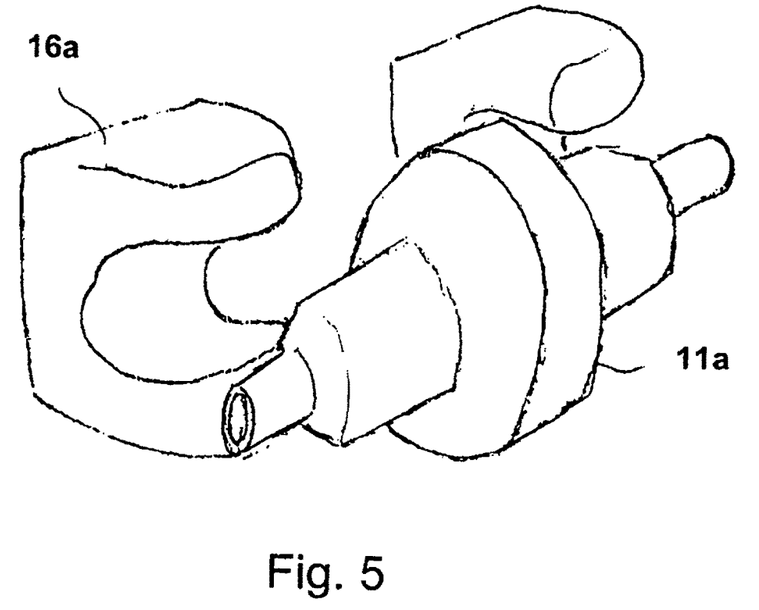

The valve body 11a in FIG. 5 in a three-dimensional view is represented as a housing which encloses the valve control space 12a as well as the feed channel 1 and the discharge channel 2, as well as the housing 16a comprising the magnet devices A' and B'. The housing 11a is separable from the housing part 16a if a part of the valve device is to be designed as a disposable valve, so that the magnet devices can be used several times or continue to be used, whereas the part of the valve which comprises the valve control space 12 can be exchanged.

FIG. 3 shows the valve according to the invention in combination with a fluid control device which is likewise according to the invention and which comprises a catheter 21, a rotating shaft 22 passing through the catheter 21, as well as a rinsing device which is not represented in detail, wherein the valve with the valve body 11a, the valve control space 12a and the mechanical parts of the valve drive forms a part of the rinsing device. Further parts of the rinsing device for example can be a rinsing agent pump and rinsing agent reservoir, which are not represented in detail. The feed channel or discharge channel 1, 2 can be connected to the catheter 21, in order to permit rinsing agent to be led into or out of the catheter by way of suitable actuation of the valve. The twisted structure of the shaft 22 is also to be recognised in FIG. 3, and this can lead to a different suction and pressure effect depending on the speed of the shaft rotation and the wearing of the shaft.

Figure 6:
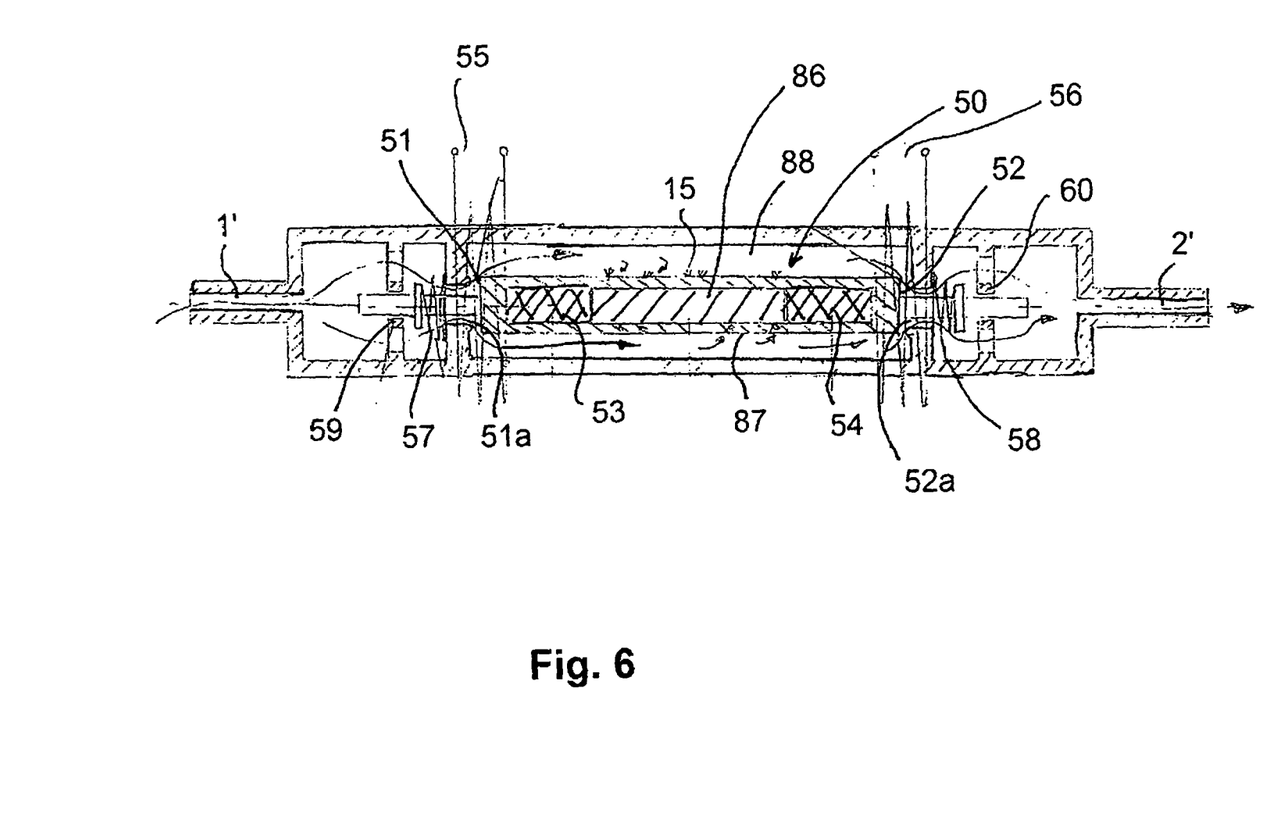

FIG. 6 shows a magnetic valve with a transport channel, through which fluid flows between a feed opening 1' and a discharge opening 2'. A closure body 50 can be driven within the transport channel 88 between a first closure position and a second closure position, wherein a first closure surface 51 closes a valve opening 51a in a first closure position, whereas a closure surface 52 closes a valve opening 52a in the second closure position.

Two armature bodies 53, 54 which can be driven by the magnetic field of two valve drive coils 55, 56 are integrated into the closure body 50. The magnet 86 of the separating device is arranged axially between the armatures bodies 53, 54 in a manner flush with these. The armature bodies with the magnet body 86 is provided with a common solid matter encasing 87. The particles which cling to the solid matter encasing 87 are indicated at 15 by way of example.

Holding springs 57, 58 in the absence of an excitation of the valve drive coils hold the closure body in a middle position, in which the valve is open. Two plain bearings 59, 60 are provided at the ends of the valve housing, for guiding the closure body 50.

Figure 7:
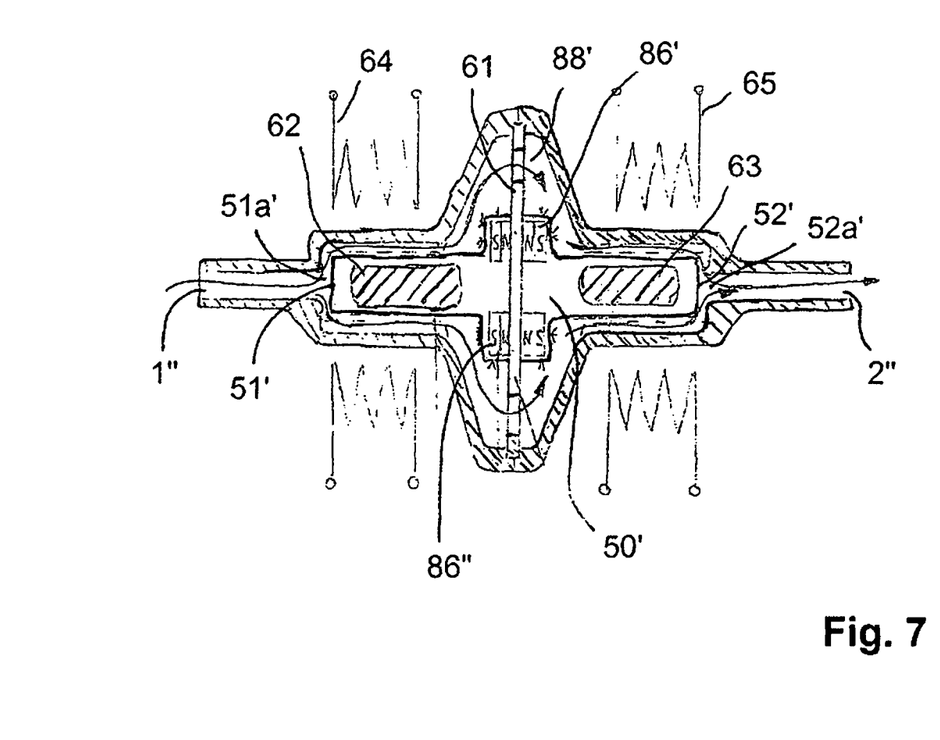

FIG. 7 shows a valve with a feed opening 1″, a discharge opening 2″ and a closure body 50′. The closure body 50′ can be driven within the transport channel 88′ between a first closure position and a second closure position, wherein a first closure surface 51′ closes a valve opening 51a′ in the first closure position, whereas a closure surface 52′ closes a valve opening 52a′ in the second closure position. The closure body 50′ is mounted in the housing of the valve by way of an elastic, permeable disc 61 and is held in an opened middle position. The disc 61 carries separating magnets 86′, 86″ which are connected in the closure body 50′ to valve drive armatures 62, 63 and together with these are enveloped by a protective layer.

The valve drive armatures 62, 63 are can be driven in the field of the coils 64, 65. Particles can accumulate in the transport channel on the separating magnets on the protective layer and can be retained there.

The catheter device 100 mentioned in the claims is now represented in the FIGS. 8-12 in several alternatives.

Figure 8:
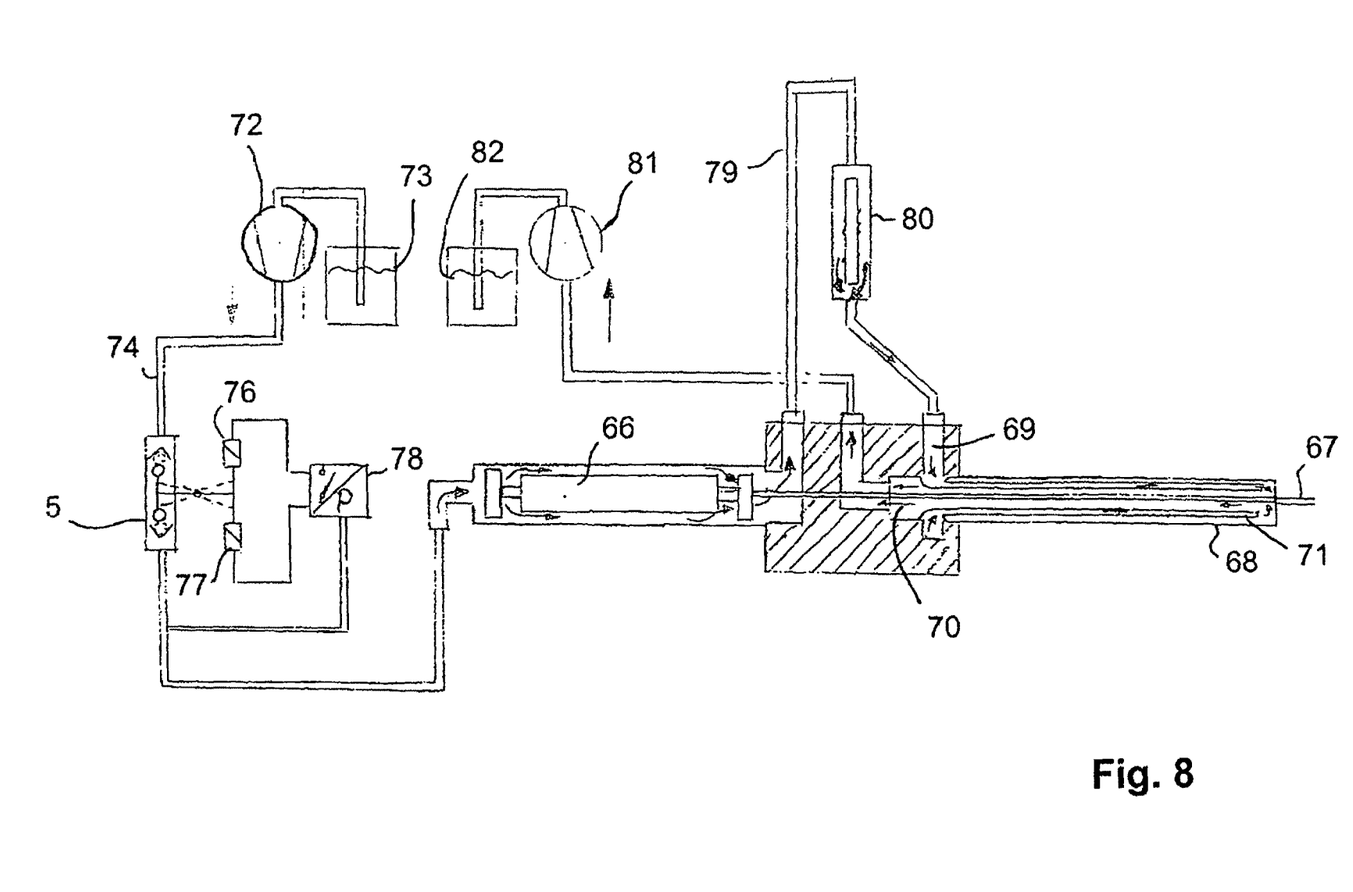

FIG. 8 shows a catheter device 100, comprising a drive unit with a drive armature 66 drivable in rotation and driving a rotating shaft 67 in a catheter 68. Lumens, designed radially to the outside as a feed channel 69 and radially to the inside as a return channel 70 are arranged concentrically to one another within the catheter 68 and to the outer envelope of the catheter. The feed channel 69 and the return channel 70 are separated from one another by a hose-like separating wall 71.

A rinsing fluid is pumped from a reservoir 73 through a lumen 74 which is designed as a cannula, and a valve 75, by way of a volume-controlled peristaltic pump 72. Two magnets 76 and 77 serve for the drive of the valve and are activated by way of a pressure switch 78 with the aim of maintaining a constant pressure in the feed channel 69. The fluid for this is led through the valve 75 and through the housing of the drive armature 66, through the lumen 79 designed as a transport channel and through the separating device 80 where particles are actively filtered out of the fluid. The separating device 80 can be constructed as the separating device shown in FIG. 6. From there, the fluid flows into the catheter 68 radially outwards through the feed channel 69 and radially inwards through the return channel 70, as well as from there to a peristaltic pump 81 which sucks the fluid and leads into the reservoir 82. The peristaltic pump 81 however can also serve for back-rinsing and for this purpose can be operated in a manner such that it delivers the fluid to the return channel 70 and from there via the feed channel 69, through the separating device back to the valve 75 into the reservoir 73, in order for example to remove the captured particles from the separating device.

Figure 9:
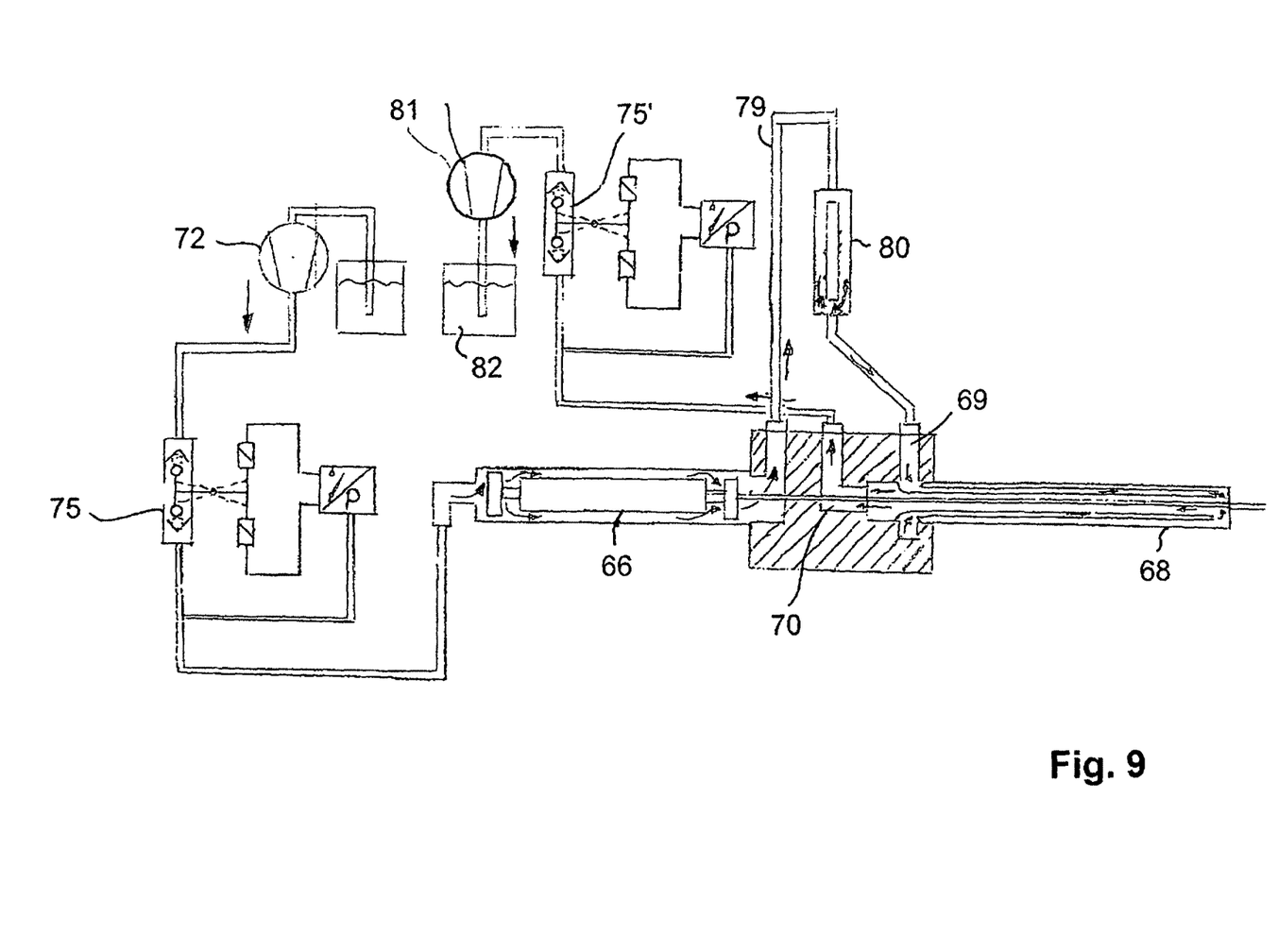
Figure 10:
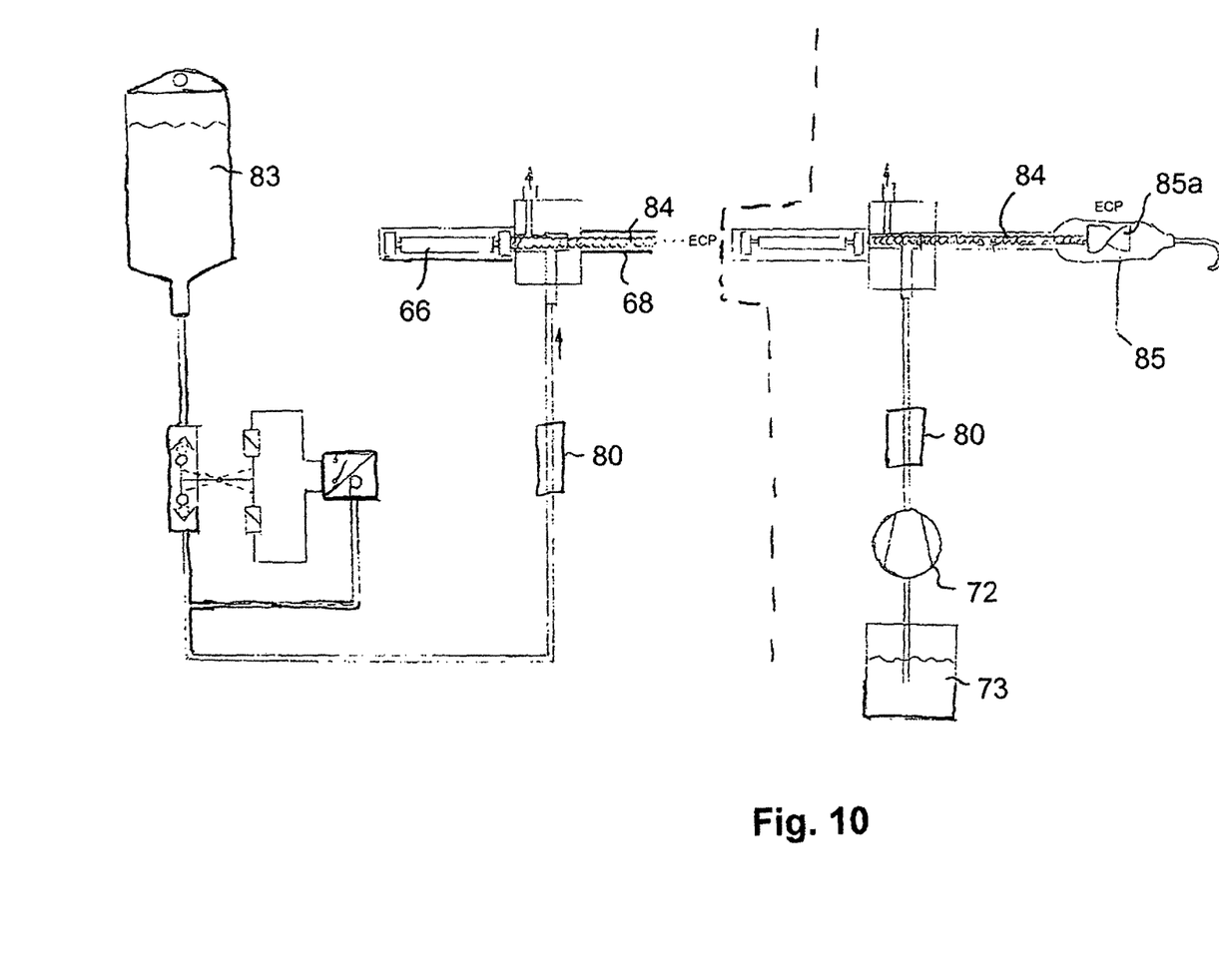

FIG. 9 shows a construction similar to that of FIG. 8, wherein additionally to the valve 75, a second valve 75′ is arranged between the return channel 70 and the return pump 80, in front of the drive armature 66 and behind the peristaltic pump 72. Whist FIG. 8 is applied with rinsing systems, in which no undesired vacuum is produced in the return due to installation components, it is possible to apply FIG. 9 also with rinsing systems, in which an undesired vacuum arises in the return (e.g. due to the winding direction of the flexible shaft). This vacuum is recognised by the sensor which then, by way of closing the valve 75′ to the bottom, ensures that no medium gets out of the container 82 via the pump 81 into the rinsing circuit. The separating device is thus arranged between two valves and also between to fluid delivery devices, of which at least one, in particular both, can be switched over with respect to the delivery direction of the fluid, in order to reverse the flow direction. With regard to the construction according to FIG. 10, in comparison to the construction in FIG. 8, it is only a peristaltic pump 72 which has been replaced by a reservoir 83 which permits a gravity flushing, by way of the fluid flowing through the valve 75 and further to the catheter 68 due to gravity. The rotating shaft 84 within the catheter 68, due to its stranded/twisted construction based on twisted strands has a helical (coiled) outer structure, which on rotation gives this itself a pumping effect in the direction away from the drive armature 66. Another variant with a volume-controlled peristaltic pump 72 and with a reservoir 73 is represented on the right side of FIG. 10, to the right of the dashed line 85, for the feed of fluid to the catheter 68. The peristaltic pump there delivers the fluid to the inside of the catheter which for example is introduced into the body of a patient and there ends at a heart pump 85 with a rotor 85a. The heart pump for example can be radially compressed which is to say as a whole can be particularly prone to particles which get therein. The fluid then flows back from there. A separating device 80 can be provided in each case upstream of the catheter 68 in the flow direction, between this and the delivery device 73, 83, in particular in any case upstream of the heart pump 85.

Figure 11:
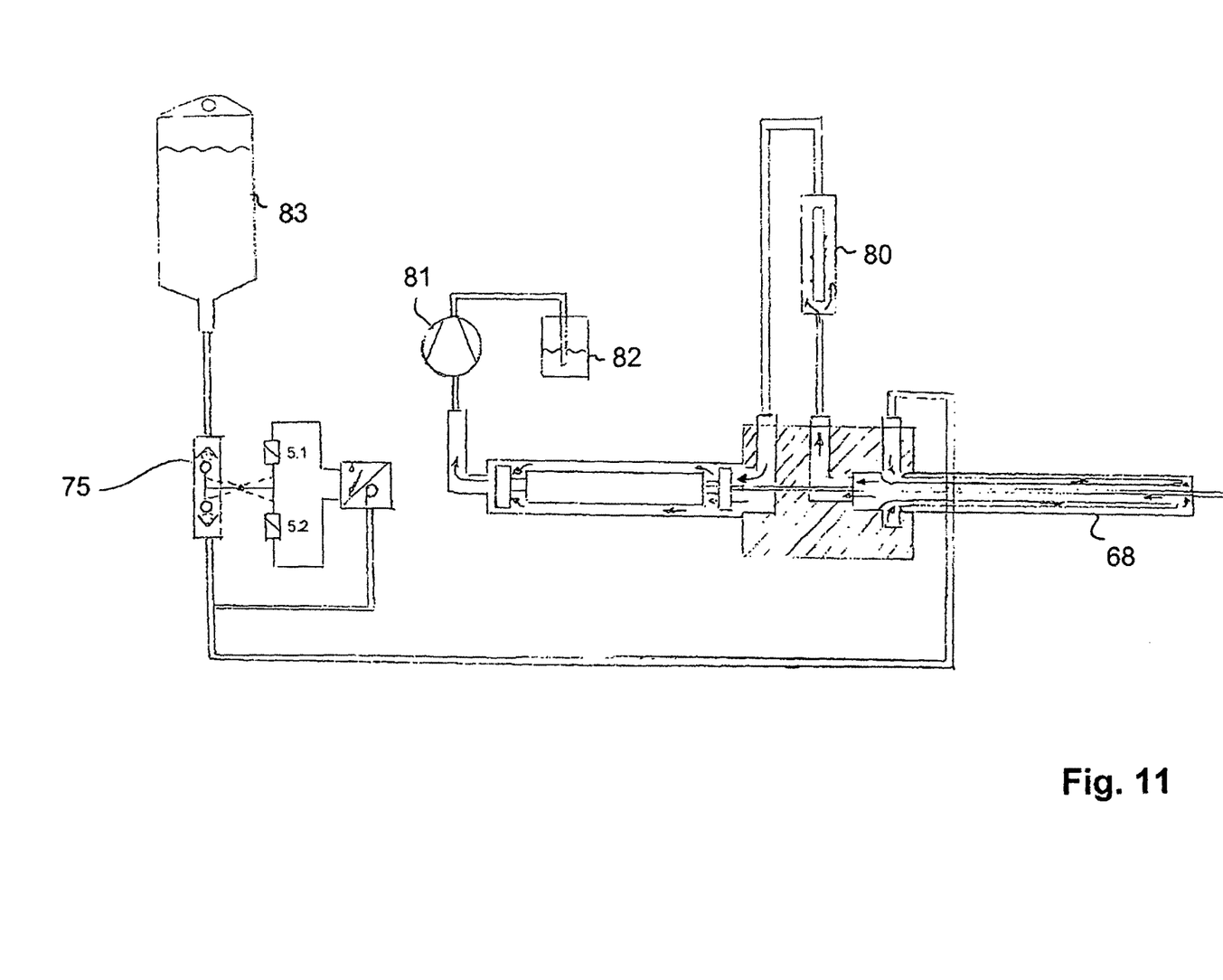

FIG. 11 shows a constellation similar to that of FIG. 9, wherein a gravity delivery 83 is envisaged instead of the peristaltic pump 72, wherein on normal operation, fluid leads from there via the valve into the catheter 68 and there firstly radially outwards through the feed channel 69, radially inwards into the return channel 70, as well as from there to a peristaltic pump 81 which sucks the fluid and leads it into the reservoir 82. The fluid between the return channel 70 and the peristaltic pump 81 firstly passes the separating device 80 which is arranged between the return channel and the housing of the drive armature 66. The fluid thereafter flows past the drive armature 66 to the peristaltic pump 81. The mounting of the drive armature can be relatively insensitive, so that the through-flow direction of the fluid there is of minor significance. What is important is that the housing of the drive armature is supplied with fluid, to ensure a good lubrication. The selected arrangement moreover ensures that magnetic wear particles of the rotating shaft 84 in this case cannot damage the bearings of the drive armature.

Figure 12:
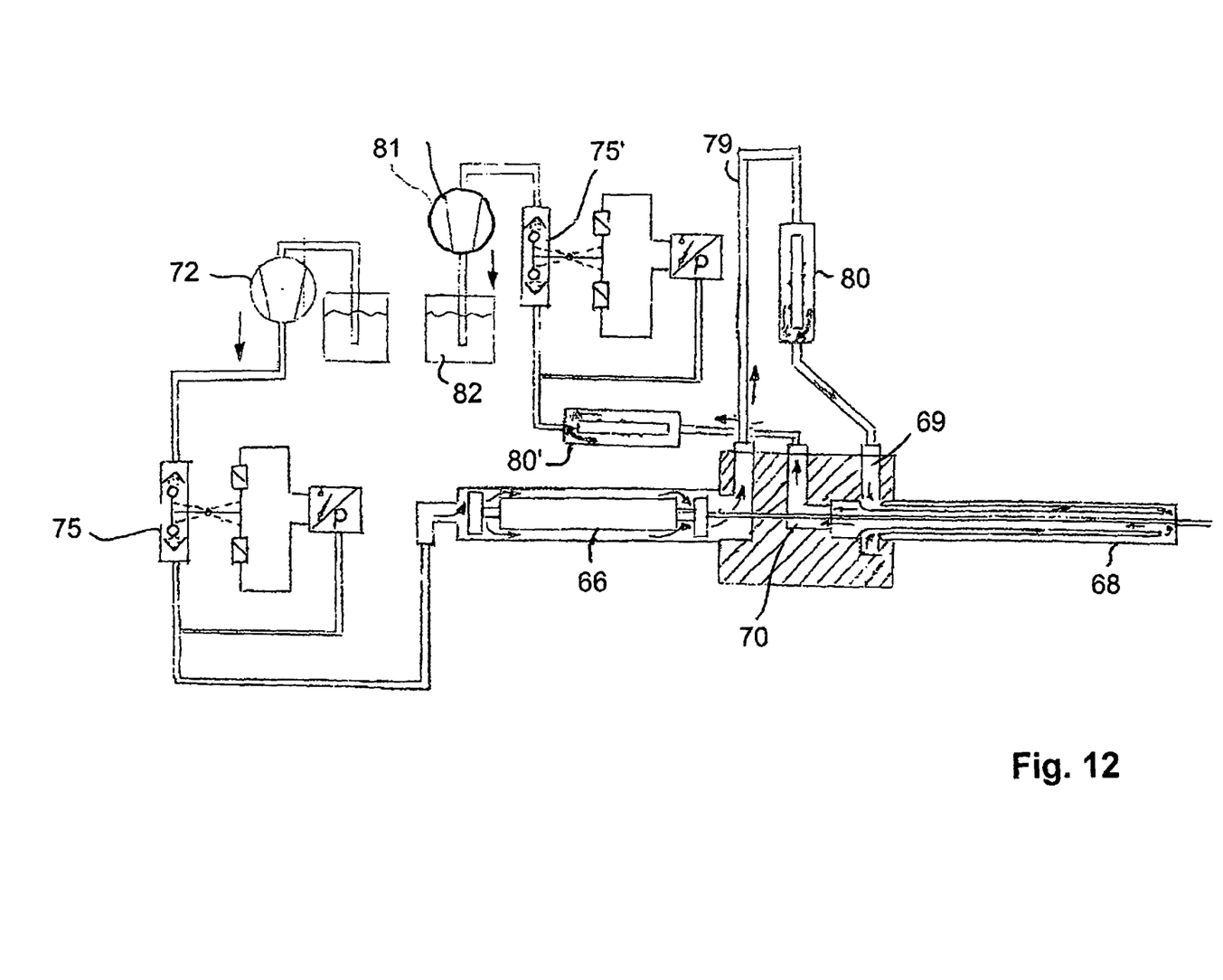

FIG. 12 shows a construction similar to FIG. 9, wherein a further separating device 80′ ensures that the function of the sealing surfaces of the valve 75′ is not compromised by clinging particles.

The present application amongst other things relates to the following aspects.

1. A valve for the control of a fluid flow, in particular through a catheter, with a valve control space (12, 12a), in which a feed channel (1) runs out with a feed opening (1a), and discharge channel (2) runs out with a discharge opening (2a), and with a closure element (5, 13, 17) which is movable in a controlled manner in the valve control space (12, 12a) and which in at least one first position (I) closes the discharge opening (2a), in at least one second position (II) closes the feed opening (1a) and in at least one third position (III) holds open a connection channel between the feed opening (1a) and the discharge opening (2a), wherein a valve drive (A, B, A', B', 3, 14, 18) is provided, which selectively moves the closure element (5, 13, 17) at least into the first, second or third position.

2. A valve according to aspect 1,
characterised in that
the third position (III) of the closure element (5, 13 17) lies between the first and the second position.

3. A valve according to aspect 1 or 2,
characterised in that
the valve control space (12, 12a) can be separated from a valve drive of the closure element (5, 13 17).

4. A valve according to aspect 1 and one of the following, characterised in that
the valve control space (12, 12a) with the exception of the feed opening (1a) and the discharge opening (2a) is closed off on all sides in a fluid-tight manner.

5. A valve according to aspect 1 or one of the following, characterised in that
the closure element (5, 13, 17) comprises a movable membrane (5) which closes off the valve control space (12) in a fluid-tight manner and is deflectable in a manner such that selectively the feed opening (1a) or the discharge opening (2a) can be closed by parts of the membrane (5).

6. A valve according to aspect 5,
characterised in that
a drive lever (3, 14) of the valve drive (3, 14, 18, A, B, B, B') deflects the membrane (5) at least in the first and second position.

7. A valve according to aspect 1 or one of the following, characterised in that
the closure element (5, 13, 17) can be driven by a magnetically acting valve drive (A, A', B, B')

8. A valve according to aspect 7,
characterised in that
the closure element (5, 13, 17) which is arranged in the valve control space (12, 12a) is magnetically active and interacts with a magnetic field of the valve drive (A, A', B, B').

9. A valve according to aspect 6 and 7,
characterised in that
the drive lever (3, 14) can be magnetically driven.

10. A valve according to aspect 7,
characterised in that
the valve control space (12, 12a) as well as the parts (3, 14, 18) of the valve drive which are mechanically connected to the closure element (5, 13, 17), with the exception of the feed and discharge opening (1a, 2a) are closed off in a fluid-tight manner and can be separated from a magnetic field production device (A, A', B, B') of the valve drive.

11. A valve according to aspect 1 or one of the following, characterised in that
the closure element is moved by an elastic spring element (10, 18), preferably into the third position (III).

12. A valve according to aspect 1 or one of the flowing, characterised in that a magnet (13", 13''', 13'''') is provided as part of a separating device, directly on the valve control space (12, 12a) in particular in the inside of the closure element (5, 15, 17).

13. A valve according to aspect 12, characterised in that the magnet/magnets (13', 13''', 13'''') are provided separately from and in particular distanced to drive armatures (53, 54, 62, 63) of the one valve drive.

14. A catheter, comprising a valve according to at least one of the preceding claims, characterised in that the valve control space can be separated from a valve drive of the closure element.

15. A protective device for a valve (75, 75') which is in connection with a flowing fluid, characterised in that a separating device (80) for holding back particles located in the fluid and with at least one magnet element (86, 86', 86") is provided along the flow channel (79, 88) for the fluid, in particular a catheter, in a manner distanced to the valve and in particular separated from this.

The invention claimed is:

1. A catheter device, comprising:
a catheter for introduction into a patient, the catheter having at least one lumen extending through the catheter configured to direct a fluid flow within the catheter device;
a valve operatively coupled to the catheter to control the fluid flow through the catheter, the valve comprising:
a valve controller, having a feed channel, a feed opening, a discharge channel, and a discharge opening, wherein the feed opening and the discharge opening are separated by a connection channel; and
a moveable closure element configured to be movable in a controlled manner in the valve controller, the moveable closure element configured to take a first position in which the discharge opening is closed, a second position in which the feed opening is closed, and a third position in which the moveable closure element holds open the connection channel; and
a valve drive configured to move the moveable closure element between the first position, the second position, and the third position,
wherein the at least one lumen is connected to the feed channel or the discharge channel and is configured to direct fluid through the feed channel or the discharge channel,
wherein the catheter further comprises a rotatable shaft, the rotatable shaft being flexible and configured to be adapted to a curvature of an aortic arch of the patient,
wherein a drive device external to the patient is configured to drive the rotatable shaft
wherein the catheter is configured as an expandable catheter pump, and
wherein the valve controller is configured to be detachable to the valve drive in a destructive-free manner, wherein at least a part of the moveable closure element is configured as a magnetic element and the valve drive comprises a magnetic field production device configured to move the moveable closure element between the first position, the second position, and the third position.

2. A catheter device according to claim 1, wherein the catheter comprises a plurality of lumens, wherein a first lumen is configured to direct a fluid in a distal direction and a second lumen is configured to direct the fluid in a proximal direction.

3. A catheter device according to claim 2, wherein the first lumen is configured to direct between 10 and 90 percent of the fluid in the distal direction and the second lumen is subsequently configured to direct the fluid in the proximal direction.

4. A catheter device according to claim 1, further comprising a drive lumen directed through at least a portion of the drive device.

5. A catheter device according to claim 1, further comprising a second valve.

6. A catheter device according to claim 1, wherein the valve is a first valve, and wherein a discharge of the first valve is directed to a feed of the drive device, and further comprising a second valve, wherein a feed of the second valve is connected to a lumen configured to direct fluid in a proximal direction.

7. A catheter device according to claim 1, wherein the third position of the moveable closure element lies between the first position and the second position.

8. A catheter device according to claim 1 wherein the valve controller is closed off on all sides in a fluid-tight manner, with the exception of the feed opening and the discharge opening.

9. A catheter device according to claim 1, wherein the moveable closure element comprises a movable membrane adapted to close off the valve controller in a fluid-tight manner and is deflectable in a manner such that the feed opening or the discharge opening are selectively closable by parts of the membrane.

10. A catheter device according to claim 9, further comprising a drive lever disposed on the valve drive and configured to deflect the membrane such that the membrane assumes one of the first position and the second position.

11. A catheter device according to claim 10, wherein the drive lever is magnetically drivable.

12. A catheter device according to claim 1, wherein the moveable closure element is configured to be driven by a magnetically acting valve drive.

13. A catheter device according to claim 12, wherein the moveable closure element is arranged in the valve controller is magnetically active and interacts with a magnetic field of the valve drive.

14. A catheter device according to claim 12, wherein the valve controller and parts of the valve drive which are mechanically connected to the moveable closure element, with the exception of the feed opening and the discharge opening are closed in a fluid-tight manner and are separable from a magnetic field producing device of the valve drive.

15. A catheter device according to claim 1, wherein the moveable closure element is configured to be moved by an elastic spring element into the third position.

16. A catheter device according to claim 1, further comprising a magnet in the inside of the moveable closure element, the magnet configured as part of a separating device.

17. A catheter device according to claim 16, further comprising a first drive armature having a first magnet and a second drive armature having a second magnet, the first drive armature and the second drive armature disposed in the valve drive at a distance from one another.

* * * * *